(12) United States Patent
Yamamori (10) Patent No.: US 10,136,839 B2
(45) Date of Patent: *Nov. 27, 2018

(54) AIRWAY ADAPTOR

(71) Applicant: NIHON KOHDEN CORPORATION, Shinjuku-ku, Tokyo (JP)

(72) Inventor: Shinji Yamamori, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/397,965

(22) Filed: Jan. 4, 2017

(65) Prior Publication Data

US 2017/0112414 A1 Apr. 27, 2017

Related U.S. Application Data

(63) Continuation of application No. 12/836,882, filed on Jul. 15, 2010, now Pat. No. 9,566,018.

(30) Foreign Application Priority Data

Jul. 16, 2009 (JP) .................................. 2009-167640
Mar. 4, 2010 (JP) .................................. 2010-047589

(51) Int. Cl.
*A61B 5/08* (2006.01)
*A61B 5/097* (2006.01)
*A61B 5/083* (2006.01)
*A61B 5/00* (2006.01)

(52) U.S. Cl.
CPC .............. *A61B 5/097* (2013.01); *A61B 5/082* (2013.01); *A61B 5/0836* (2013.01); *A61B 5/682* (2013.01); *A61B 5/6803* (2013.01); *A61B 5/6819* (2013.01)

(58) Field of Classification Search
CPC ................................ A61B 5/097; A61B 5/087
USPC ........................................ 600/529, 532, 543
See application file for complete search history.

(56) References Cited

U.S. PATENT DOCUMENTS

| 7,162,921 B2 | 1/2007 | Gerder et al. |
| 2002/0122746 A1 | 9/2002 | Yamamori et al. |
| 2006/0042638 A1 | 3/2006 | Niklewski et al. |
| 2006/0247551 A1 | 11/2006 | Yamamori et al. |
| 2008/0196715 A1 | 8/2008 | Yamamori |
| 2008/0283062 A1 | 11/2008 | Esposito, Jr. |

(Continued)

FOREIGN PATENT DOCUMENTS

| DE | 200 01 995 U1 | 7/2000 |
| JP | 2003-315264 A | 11/2003 |

(Continued)

OTHER PUBLICATIONS

Office Action issued in European Patent Application No. 10 169 671 dated Oct. 5, 2016.

(Continued)

*Primary Examiner* — Puya Agahi
(74) *Attorney, Agent, or Firm* — Pearne & Gordon LLP (57) ABSTRACT

An airway adaptor includes: an airway case; and an expired gas guiding portion which is connected to the airway case to introduce a respiratory gas to the airway case. The airway case includes: a first respiratory gas flow path in which the respiratory gas flows in a first direction; and a second respiratory gas flow path in which the respiratory gas flows in a second direction opposite to the first direction.

21 Claims, 11 Drawing Sheets

(56) References Cited

U.S. PATENT DOCUMENTS

| | | |
|---|---|---|
| 2008/0319334 A1 | 12/2008 | Yamamori |
| 2009/0069646 A1 | 3/2009 | Yamamori et al. |
| 2009/0187111 A1 | 7/2009 | Reilly, Jr. et al. |
| 2009/0275852 A1* | 11/2009 | Oki .................. A61B 5/097 |
| | | 600/532 |

FOREIGN PATENT DOCUMENTS

| | | |
|---|---|---|
| JP | 2008-200061 A | 9/2008 |
| JP | 2009-066431 A | 4/2009 |

OTHER PUBLICATIONS

Macmillan dictionary: opposite; in U.S. Appl. No. 12/836,882 Office Action dated Apr. 8, 2016.
Japanese Office Action issued in Patent Application No. 2010-047589 dated Jun. 21, 2011.
Extended European Search Report issued in Patent Application No. EP 10 16 9671 dated Nov. 10, 2010.

\* cited by examiner

AIRWAY ADAPTOR

BACKGROUND OF THE INVENTION

The present invention relates to the shape of an airway adaptor for, in carbon dioxide measurement for detecting and measuring the existence, concentration, and the like of carbon dioxide in the respiratory gas expired through the nostrils or mouth of the living body, guiding the expired gas discharged through the nostrils or mouth of the living body, thereby allowing a measurement relating to carbon dioxide in the expired gas to be effectively performed. The airway adaptor is configured so that, in the case where a carbon dioxide sensor is to be attached to the airway adaptor, the operations of attaching or detaching the sensor can be performed simply and easily.

For example, a related-art carbon dioxide sensor for detecting and measuring the existence, concentration, and the like of carbon dioxide in the expired gas discharged through the nostrils or mouth of the living body is configured in the following manner (see JP-A-2003-315264). An airway case is provided in which transmissive windows through which light is transmitted are disposed on right and left side faces of an airtight case that is formed in a cylindrical or box-like shape, respectively, and openings for guidingly introducing the expired gas and leading the gas to the outside are formed in the upper and lower faces or the like, respectively. On the side faces of the airway case in which the transmissive windows are disposed, a light emitting element and a light receiving element are supported by supporting members, respectively while being opposed to each other. Light which is transmitted through the expired gas passing through the interior of the airway adaptor is detected and measured.

In order to effectively introduce the expired gas discharged through the nostrils of the living body into the airway case for attaching the carbon dioxide sensor, the airway adaptor is configured so that one side has nasal tubes which are to be inserted respectively into the two nostrils of the living body, and the other side is connected to a hole portion disposed in the airway case. The carbon dioxide sensor is configured so as to be detachable from the airway case.

In the thus configured carbon dioxide sensor, the measurement object is the expired gas discharged through the nostrils of the living body, and therefore the nasal tubes are attached to the nostrils with using an airway adaptor. Accordingly, the sensor can be applied also to a mask which is configured as a mask for carbon dioxide measurement having a nasal mask shell.

From this viewpoint, a related-art carbon dioxide nasal mask has been developed, which, even when a gas is supplied at a high flow rate from the outside into the mask, can correctly measure the concentration of carbon dioxide, and which is configured so that oxygen or the like can be forcibly supplied (see JP-A-2008-200061).

Namely, the carbon dioxide nasal mask disclosed in JP-A-2008-200061 includes: a nasal mask shell which has a close contact edge adapted to be brought into close contact with the face so as to cover the nose, and the interior of which configures a sealed space; an airway case which is formed in a part of the nasal mask shell, which, in a state where the nasal mask shell is worn, is positioned immediately below the nostrils, thereby allowing the expired gas expired through the nostrils to be introduced, which has an expired gas discharge port for discharging the introduced expired gas, and which is used for detachably attaching a carbon dioxide sensor to the outside of the nasal mask shell; an introduction port for allowing a gas such as oxygen or air to be introduced from the outside into the nasal mask shell; and a nasal tube for ensuring a passage through which, in the nasal mask shell, the expired gas that is introduced from the nostrils into the airway case is guided to the airway case without being diluted by the gas arriving from the introduction port.

In the thus configured carbon dioxide nasal mask, the expired gas reaches the airway case through the nasal tube, and adequately escapes into the nasal mask shell through the expired gas discharge port. Even when oxygen or the like arrives at the introduction port disposed in the nasal mask shell, therefore, accurate carbon dioxide measurement is enabled without causing the expired gas from the nose to be diluted by oxygen or the like which flows into from the introduction port. Since the nasal mask shell is in close contact with the face in the close contact edge, the oxygen or the like arriving at the introduction port can be used for generating a positive pressure, and hence can be used in an apparatus for CPAP (Continuous Positive Airway Pressure) or NPPV (Noninvasive Positive Pressure Ventilation) therapy which is used in treatment of a patient suffering from sleep apnea syndrome or respiratory failure. Therefore, carbon dioxide measurement under positive pressure ventilation which is hardly performed in the prior art is enabled.

In JP-A-2008-200061, the airway case which is disposed in the carbon dioxide nasal mask, and which is used for attaching the carbon dioxide sensor is formed as a part of the nasal mask, the Y-shaped nasal tube which can be inserted into the nostrils is disposed in one end of the airway case, and the other end is disposed so as to be opposed to an open port disposed in the airway case. With respect to the thus configured airway case, it is necessary to obtain a configuration arrangement where the inlet and outlet for the expired gas are disposed so as to be opposed to each other, and, in order to allow the introducing flow of the expired gas to easily move, the whole airway case is housed inside the carbon dioxide nasal mask.

As described above, the carbon dioxide nasal mask has a complex design, and hence works such as assembling of a plurality of parts and maintenance are required. When the mask and the airway case are made detachable without causing air leakage, there arises a problem in that the structure is complicated. Also in the case where the carbon dioxide sensor is attached to the airway case, the sensor must be incorporated inside the nasal mask, and there is a disadvantage in that the attaching and detaching operations are cumbersome.

Moreover, the carbon dioxide nasal mask has a special shape which is complexly designed, and hence is difficult to be produced. Therefore, problems in production technique and cost remain to be solved.

SUMMARY

It is therefore an object of the invention to provide an airway adaptor configured so that operations of attaching and detaching a carbon dioxide nasal mask (or a carbon dioxide face mask), to and from an expired gas guiding portion and an airway case are facilitated, the airway case is configured so as to be projected to the outside of the nasal mask (or the face mask), a hermetical configuration is formed in which introduction and discharge of the expired gas passing through the airway case can be surely performed inside the nasal mask (or the face mask) without causing air leakage to the outside thereof, and a carbon dioxide sensor can be easily attached to and detached from the airway case.

In order to achieve the object, according to the invention, there is provided an airway adaptor comprising:

an airway case; and an expired gas guiding portion which is connected to the airway case to introduce a respiratory gas to the airway case, wherein the airway case includes:

a first respiratory gas flow path in which the respiratory gas flows in a first direction; and a second respiratory gas flow path in which the respiratory gas flows in a second direction opposite to the first direction.

The expired gas guiding portion may be detachably connected to the airway case.

The airway case may include a first side face and a second side face which are opposed to each other, and a carbon dioxide sensor may be attachable to the first side face and the second side face.

The first respiratory gas flow path and the second respiratory gas flow path may be juxtaposed to each other.

One of the first and second respiratory gas flow paths may surround the other of the first and second respiratory gas flow paths.

A nose cup for surrounding a periphery of nostrils may be disposed on one of the expired gas guiding portion and the airway case.

A part of the airway adaptor may be disposed on a nasal mask shell of a nasal mask in which positive pressure ventilation is enabled, and the airway case may be projected to an outside of the nasal mask shell.

The expired gas guiding portion may be a nasal tube which is to be inserted into nostrils of a living body.

The expired gas guiding portion may include: a first guiding portion which guides the respiratory gas from nostrils of a living body; and a second guiding portion which guides the respiratory gas from a mouth of the living body.

The respiratory gas which is guided by the first guiding portion and the respiratory gas which is guided by the second guiding portion may be joined together in the airway case or at an upstream side of the airway case.

A part of the airway adaptor may be disposed on a face mask shell of a face mask in which positive pressure ventilation is enabled, and the airway case may be projected to an outside of the face mask shell.

The first guiding portion may be a nasal tube which is to be inserted into the nostrils of the living body.

BRIEF DESCRIPTION OF THE DRAWINGS

FIGS. 6A and 6B illustrate relationships between the configurations of first and second respiratory gas flow paths, and the flow of the respiratory gas in an airway case of the airway adaptor.

DETAILED DESCRIPTION OF EMBODIMENTS

Next, embodiments of the airway adaptor of the invention will be described in detail with reference to the accompanying drawings. In the figures, the identical components are denoted by the same reference numerals, and duplicated description will be omitted.

Figure 1:
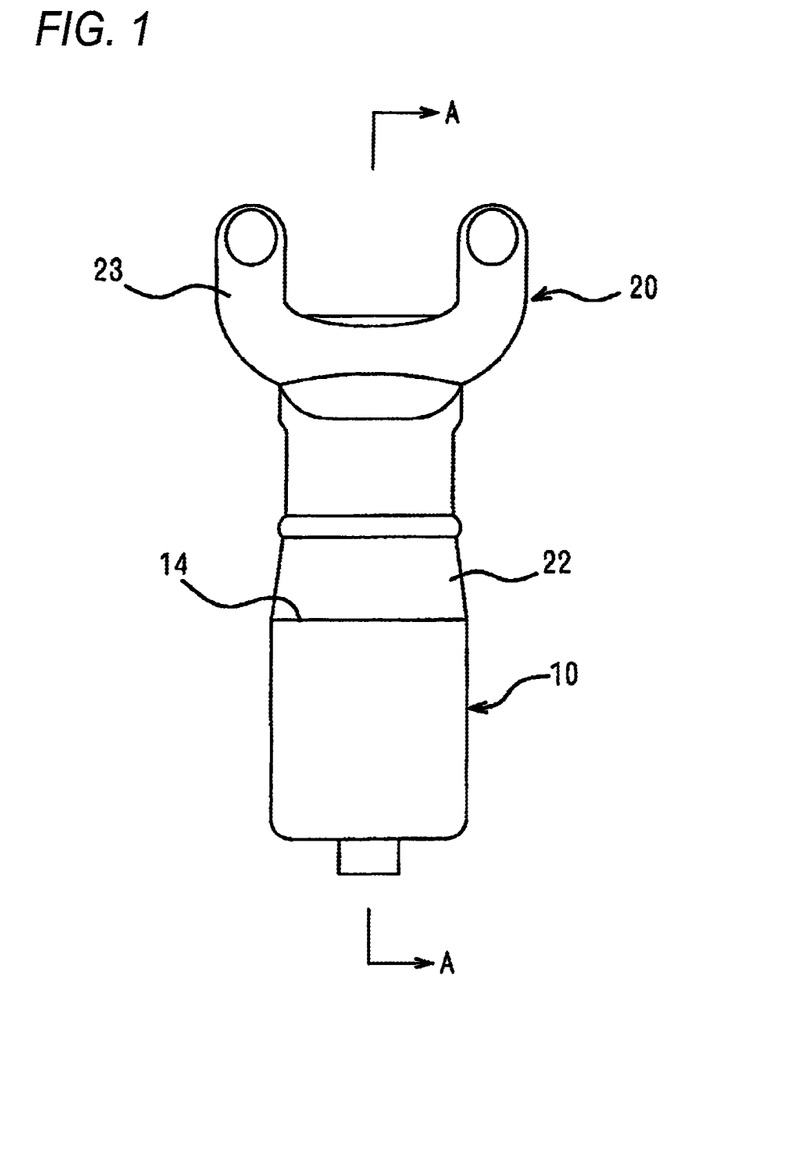
FIG. 1 is a front view showing a configuration example of an airway adaptor of the invention.
Figure 2:
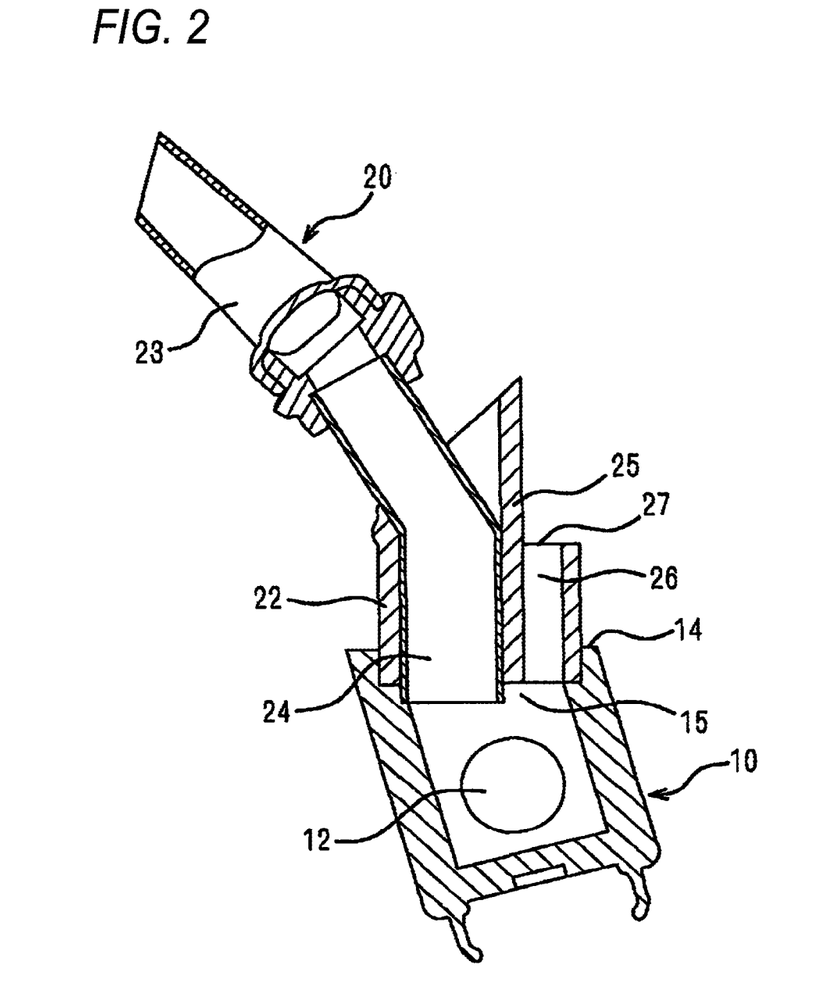
FIG. 2 is a sectional view of the airway adaptor shown in FIG. 1, taken along line A-A.

FIGS. 1 and 2 show a configuration example of the airway adaptor of the invention, FIG. 1 is a front view, and FIG. 2 is a sectional view.

Referring to FIGS. 1 and 2, the airway adaptor of the invention is configured by an airway case 10, and an expired gas guiding portion 20 which is communicatingly connected to the airway case 10 to guidingly introduce the respiratory gas to the airway case 10. The airway case 10 and the expired gas guiding portion 20 are detachably configured.

The airway case 10 includes a joining portion 22 which is used for communicating connection to the expired gas guiding portion 20, and is configured so that transmissive windows 12 through which light is transmitted are disposed on right and left side faces of an airtight case that is formed in a cylindrical or box-like shape, respectively, and an opening 15 for guidingly introducing the expired gas and discharging the gas to the outside is formed in the upper face 14.

In the expired gas guiding portion 20, a Y-shaped nasal tube 23 which is to be inserted into the nostrils of the living body is disposed in one side, and the other side is communicatingly connected to the joining portion 22 which is formed so as to be communicatingly connected to the opening 15 formed in the upper face 14 of the airway case 10 to guidingly introduce the expired gas into the airway case 10.

The airway case 10 has a configuration where an expired gas introducing passage 24 which is used for introducing the expired gas guidingly introduced from the expired gas guiding portion 20, and which functions as a first respiratory gas flow path, and an expired gas discharging passage 26 functioning as a second respiratory gas flow path which is formed so as to be juxtaposed with the expired gas introducing passage 24 to discharge the expired gas introduced into the airway case 10, to the outside are disposed. The reference numeral 27 denotes a discharge port of the expired gas discharging passage 26.

Figure 3:
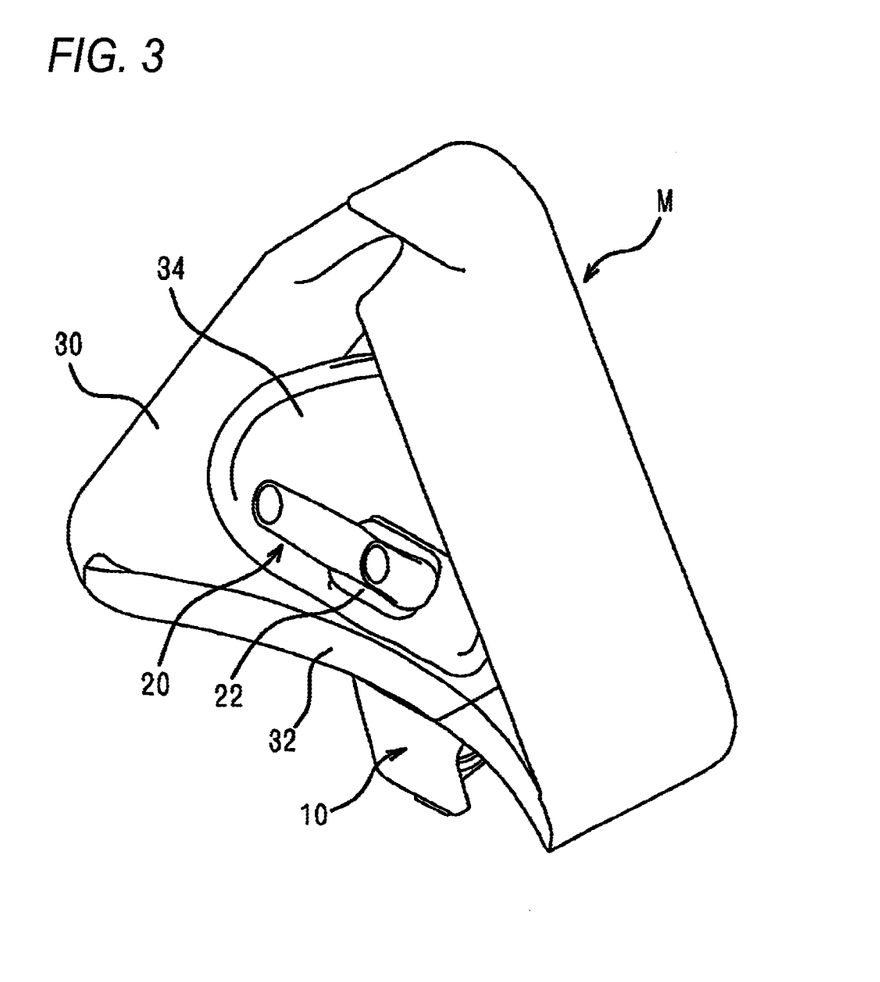
FIG. 3 is a perspective view showing an embodiment in which the airway adaptor is applied to a carbon dioxide nasal mask.
Figure 4:
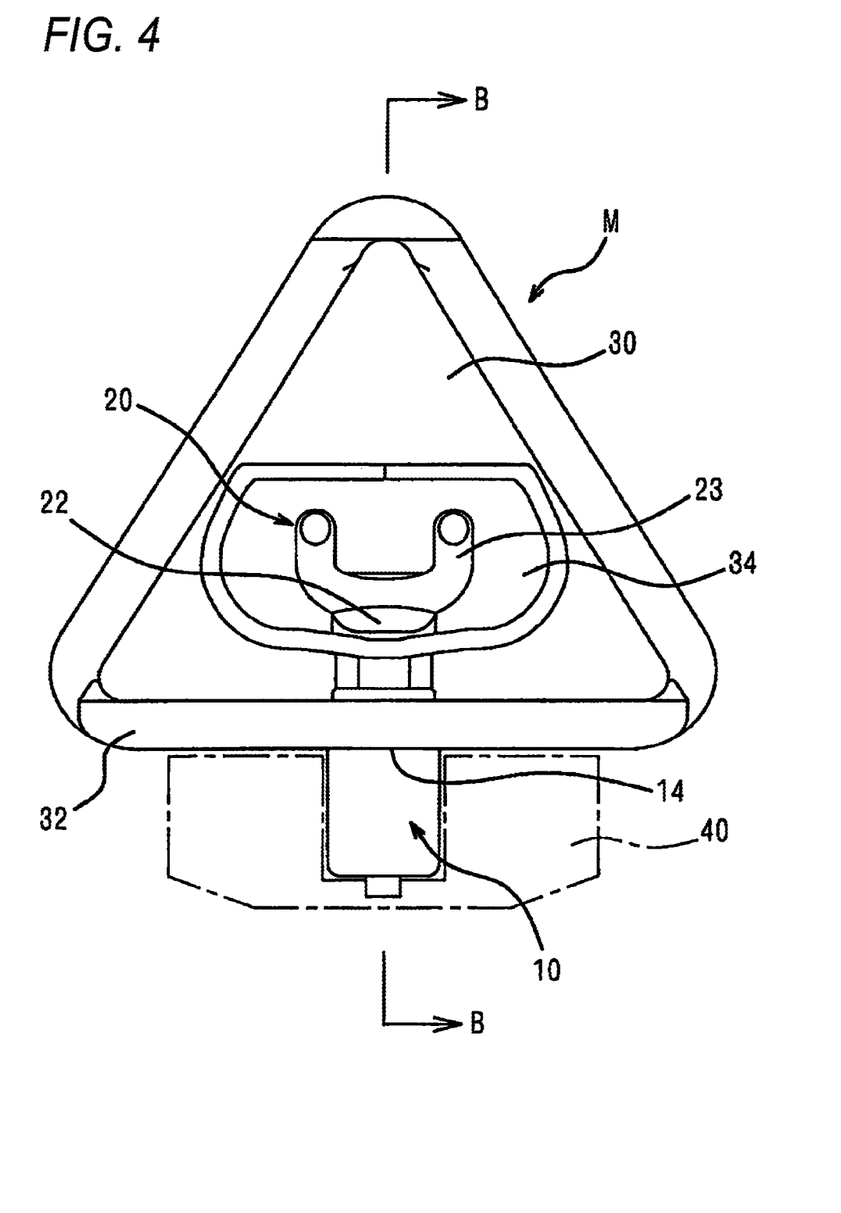
FIG. 4 is a front view of the airway adaptor which is applied to the carbon dioxide nasal mask shown in FIG. 3.
Figure 5:
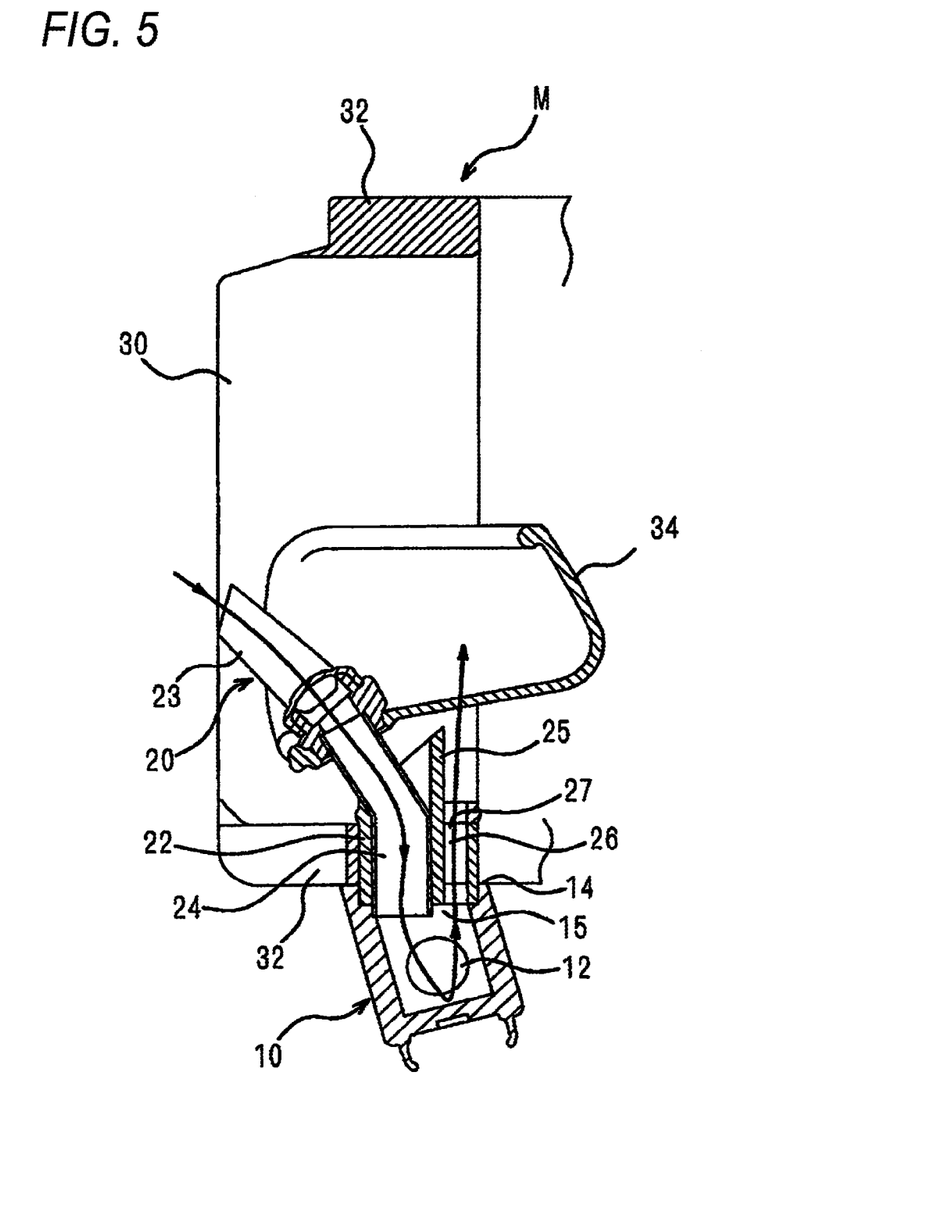
FIG. 5 is a sectional view of portions taken along line B-B of FIG. 4 and showing the configuration of the airway adaptor.

FIGS. 3 to 5 show an embodiment in which the thus configured airway adaptor of the invention is applied to an outer edge portion of a nasal mask shell constituting a nasal mask, FIG. 3 is a perspective view, FIG. 4 is a front view, and FIG. 5 is a sectional view.

In FIGS. 3 to 5, as the expired gas guiding portion 20 of the airway adaptor, a nasal tube 23 which is to be inserted into the nostrils is exemplarily shown. In this case, the expired gas guiding portion 20 is requested to have a shape which can adequately guide the expired gas from the nostrils to the joining portion 22, and not required to be the nasal tube 23. For example, the portion may have a cup-like shape which covers the nostrils.

The airway case 10 may be partitioned into at least two passages by a partition wall 25 on the side of the opening 15 formed in the upper face 14, one of the partitioned passages is formed as the expired gas introducing passage 24, and the other passage is formed as the expired gas discharging passage 26 (see FIG. 5).

Figure 6A:
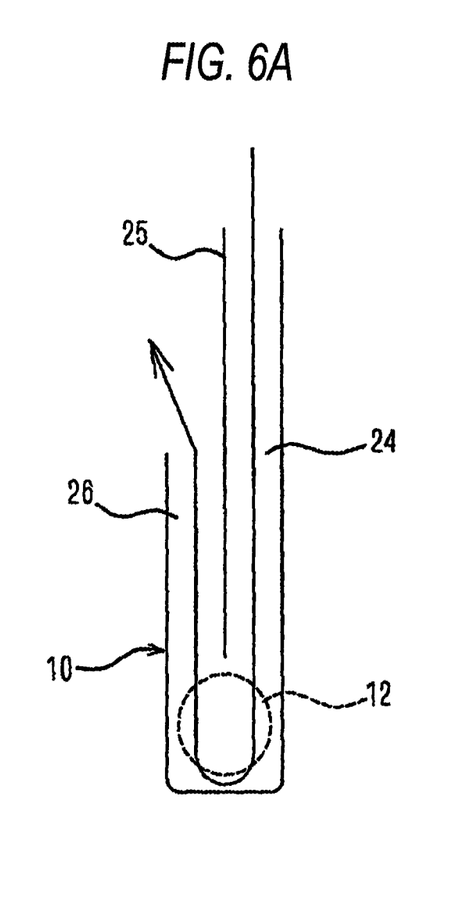
FIG. 6A is a diagram showing a configuration where the first and second respiratory gas flow paths are juxtaposed.
Figure 6B:
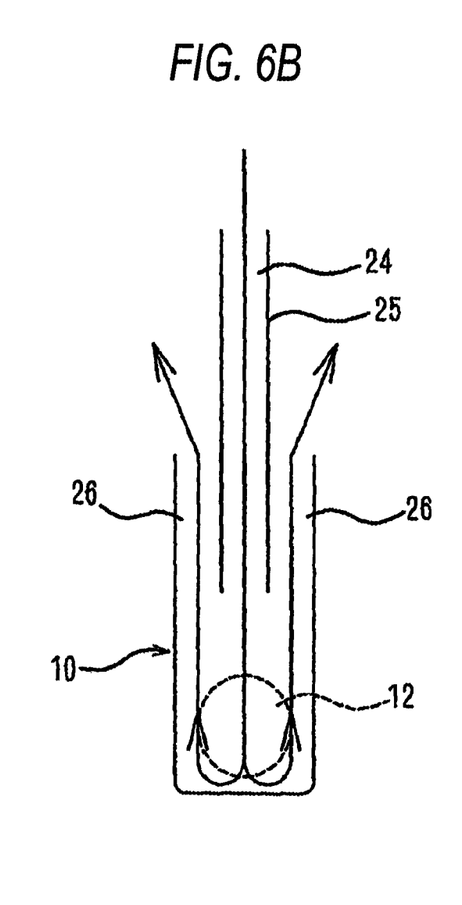
FIG. 6B is a diagram showing a configuration where one of the first and second respiratory gas flow paths surrounds the other path.

For example, the airway case 10 may be structured so that the expired gas flowing through the expired gas introducing passage 24 is returned in the airway case 10 and flows through the expired gas discharging passage 26 (see FIG. 6A). Alternatively, the airway adaptor may have a configuration where one of the expired gas introducing passage 24 and the expired gas discharging passage 26 is placed in the periphery of the other passage while being separated therefrom by a required partition wall 25' (see FIG. 6B). In this way, it may be configured so that one of the expired gas introducing passage 24 functioning as the first respiratory gas flow path and the expired gas discharging passage 26 functioning as the second respiratory gas flow path surrounds the other passage. Contrary to FIG. 6A, the expired gas introducing passage 24 may surround the expired gas discharging passage 26. As described above, it is configured (set) so that the respiratory gas flowing through the expired gas introducing passage 24 functioning as the first respiratory gas flow path, and that flowing through the expired gas discharging passage 26 functioning as the second respiratory gas flow path flow in opposite directions.

In the embodiment, in the thus configured airway adaptor, a part of the airway case 10 is fixedly placed on an outer edge portion 32 of a nasal mask shell 30 constituting a carbon dioxide nasal mask M, and the airway case 10 is connected to the outside of the outer edge portion 32 of the nasal mask shell 30 while the airway case 10 is projected from the nasal mask shell 30 as illustrated (see FIGS. 3 to 5). As illustrated, a nose cup 34 for surrounding the periphery of the nostrils of the living body is fixedly placed on a part of the airway case 10 forming the expired gas introducing passage 24 (see FIGS. 3 to 5).

In the embodiment, the discharge port 27 of the expired gas discharging passage 26 of the airway case 10 is opened in the inner side of the nasal mask shell 30. As shown in FIG. 4, a carbon dioxide sensor 40 can be detachably attached to the airway case 10 of the thus configured airway adaptor so as to be opposed to the side faces in which the transmissive windows 12 are disposed.

Figure 7:
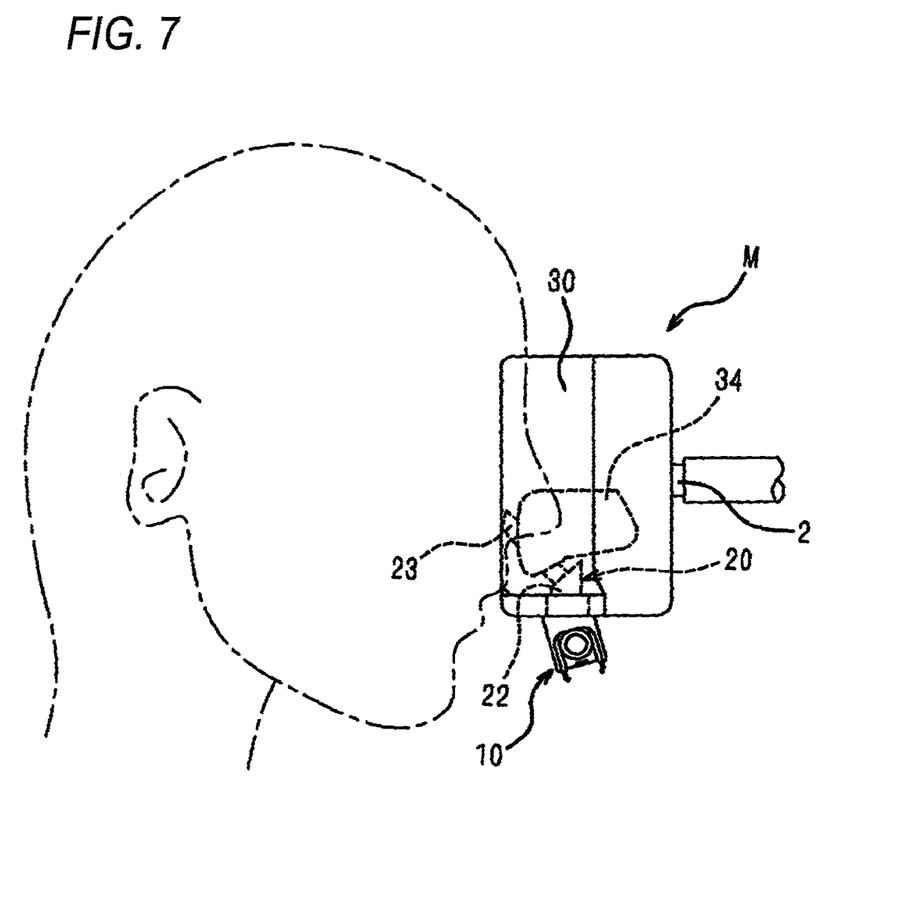
FIG. 7 is a diagram showing a use state in the case where the airway adaptor is applied to a carbon dioxide nasal mask.

FIG. 7 shows a state where the carbon dioxide nasal mask M configured by applying the airway adaptor of the embodiment is used on the subject. In this case, the outer edge portion 32 of the nasal mask shell 30 of the carbon dioxide nasal mask M butts against the periphery of the nose in the face of the subject so as to surround the periphery, the nose cup 34 is placed so as to surround a peripheral portion of the nostrils, and the tip ends of the expired gas guiding portion 20 are inserted into the nostrils, respectively. The nasal mask shell 30 is in close contact with the face in the outer edge portion 32, and hence the oxygen or the like arriving at an introduction port 2 can be used for generating a positive pressure.

In this way, the expired gas discharged through the nostrils of the subject is guidingly introduced from the expired gas guiding portion 20 to the airway case 10 through the expired gas introducing passage 24 of the airway case 10. Then, the expired gas which is introduced into the airway case 10 is discharged into the nasal mask shell 30 through the discharge port 27 which is opened in the inner side of the nasal mask shell 30 (see FIG. 5). The expired gas which is passed through the interior of the airway case 10 as described above can be subjected to detection and measurement of the concentration of carbon dioxide or the like of the expired gas, by the carbon dioxide sensor 40.

Furthermore, another embodiment of the airway adaptor of the invention in which the invention is applied to a face mask will be described with reference to FIGS. 8 to 11.

Figure 8:
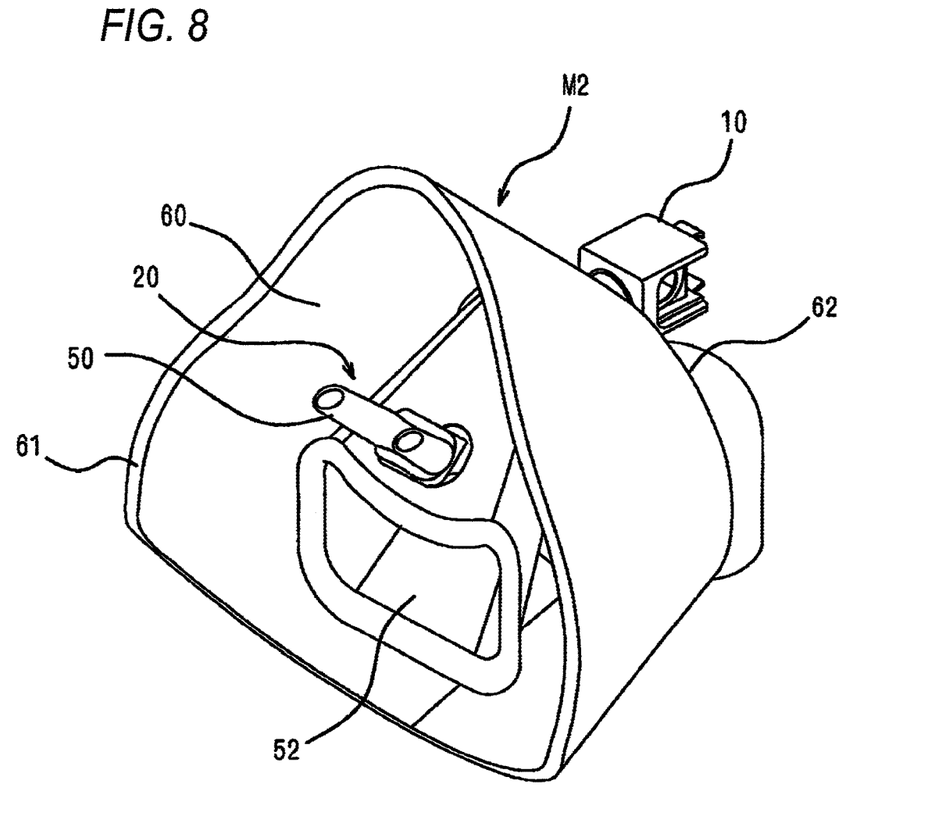
FIG. 8 is a schematic view in the case where the airway adaptor is applied to a carbon dioxide face mask.

FIG. 8 is a schematic view of a carbon dioxide face mask M2 in which the airway adaptor of the invention is applied to a face mask for covering the nose and the mouth. The carbon dioxide face mask M2 includes a face mask shell 60 having an outer edge portion 61 constituting an opening which allows the nose and mouth of the subjected to be covered. The expired gas guiding portion 20 which communicates with the airway case 10 is disposed in the face mask shell 60. The expired gas guiding portion 20 is configured by a first guiding portion 50 which guides the respiratory gas from the nostrils, and a second guiding portion 52 which guides the respiratory gas from the mouth. Although a nasal tube is shown as an example of the first guiding portion 50, the portion may be a cup-like nose cup which covers the nose. A part of the airway adaptor is fixedly placed on a tip end portion 62 in which the diameter is reduced in a tapered manner with starting from the opening configured by the outer edge portion 61 of the face mask shell 60, and the airway case 10 is projected to the outside of the face mask shell 60. Both the above-described configuration including the face mask shell 60, and a configuration from which the face mask shell 60 is omitted can be commercially distributed.

Figure 9:
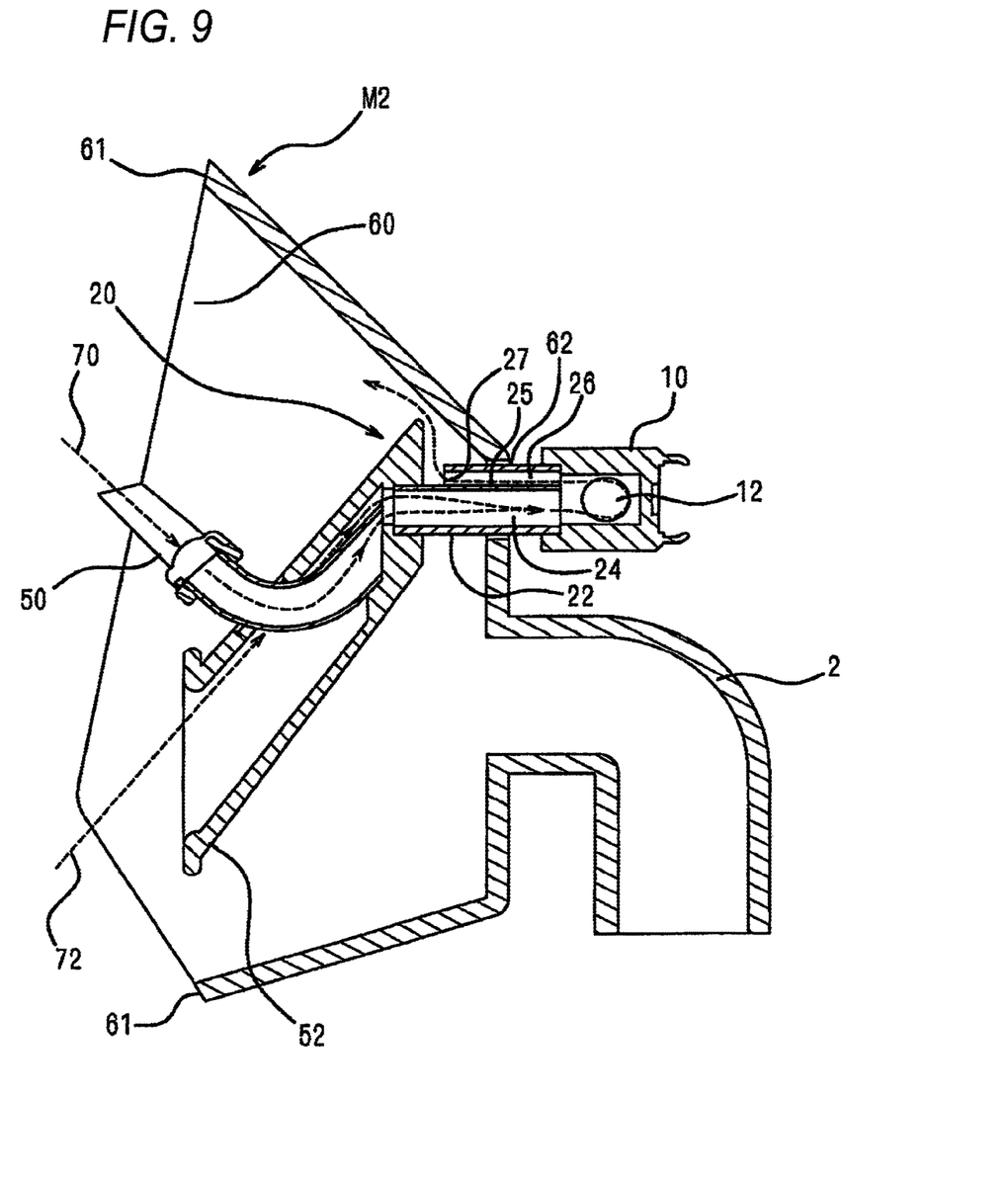
FIG. 9 is a diagram showing flows of the respiratory gases from the nose and the mouth in the case where the airway adaptor is applied to a carbon dioxide face mask.

FIG. 9 shows flows of the respiratory gas in the case where the airway adaptor of the invention is applied to a face mask. The respiratory gas 70 from the nose is guided through the first guiding portion 50, and then mixed with the respiratory gas 72 from the mouth in the joining portion 22 which is at the upstream (the upstream in the flow of the expired gas) side of the airway case 10. The mixed respiratory gas is passed through the expired gas introducing passage 24 to be guided to the airway case 10, and then discharged into the face mask through the expired gas discharging passage 26. Alternatively, the respiratory gas 70 from the nose and the respiratory gas 72 from the mouth are mixed with each other in the airway case 10.

Figure 10:
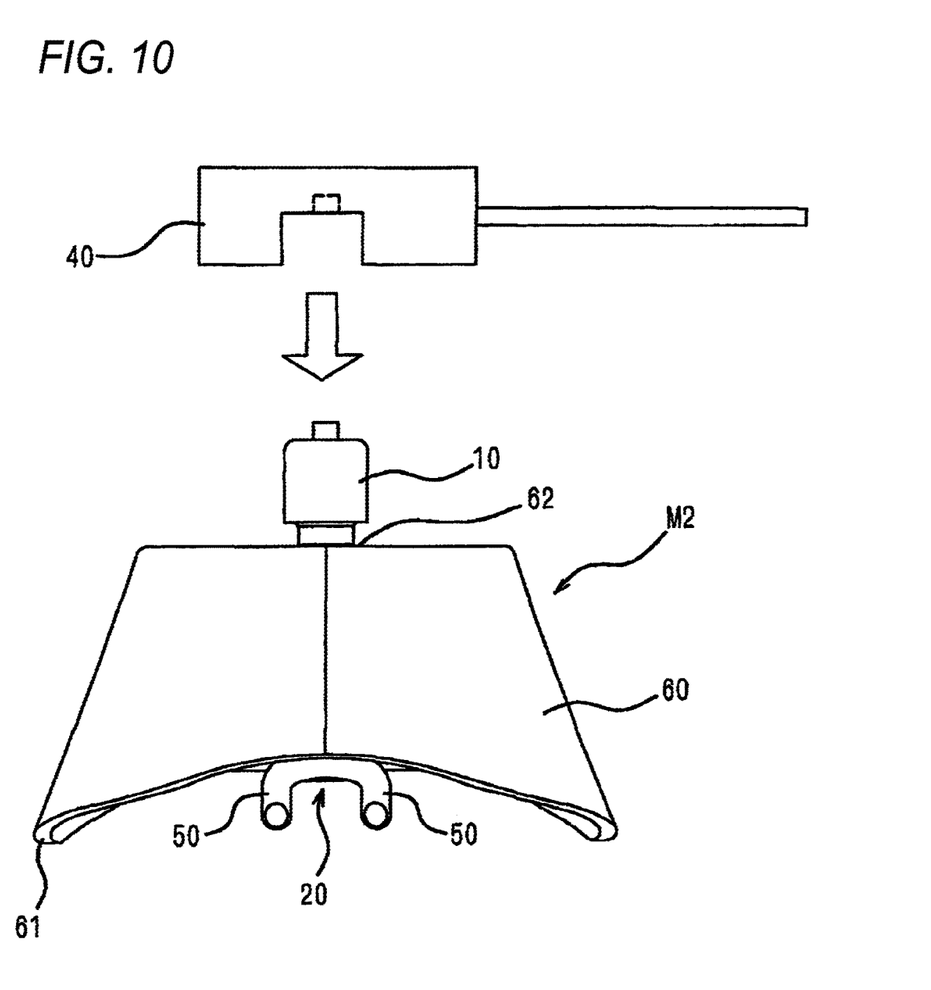
FIG. 10 is a diagram showing attachment of a carbon dioxide sensor in the case where the airway adaptor is applied to a carbon dioxide face mask.
Figure 11:
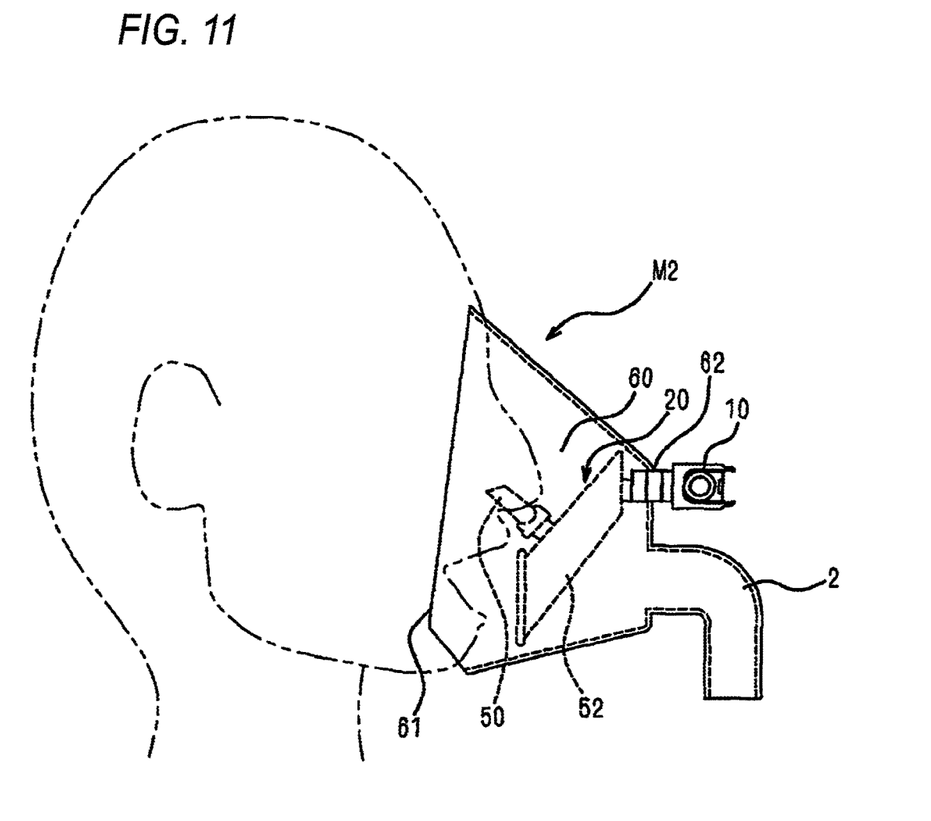
FIG. 11 is a diagram showing a use state in the case where the airway adaptor is applied to a carbon dioxide face mask.

FIG. 10 shows attachment of a carbon dioxide sensor in the case where the airway adaptor of the invention is applied to a face mask, and FIG. 11 shows a state where the sensor is used for the subject. As seen from FIG. 10, the carbon dioxide sensor 40 can be detachably attached to the airway case 10 of the airway adaptor. As shown in FIG. 11, the sensor is used while the outer edge portion 61 of the face mask shell 60 is properly closely contacted with the face of the subject. According to the configuration, it is possible to adequately detect and measure the existence, concentration, and the like of carbon dioxide in the expired gas discharged through the nostrils or mouth of the living body. The face mask shell 60 is in close contact with the face in the outer edge portion 61, and hence the oxygen or the like arriving at the introduction port 2 can be used for generating a positive pressure.

Although the preferred embodiments of the invention have been described, the invention is not restricted to the above-described embodiments. For example, the formation of the expired gas introducing passage 24 functioning as the first respiratory gas flow path and the expired gas discharging passage 26 functioning as the second respiratory gas flow path in the airway case 10 may be performed by, in place of the disposition of the partition wall 25 as in the embodiment, any one of various other configurations, as far as the passages are juxtaposed to each other. In addition, various design changes may be made without departing the spirit of the invention.

According to an aspect of the invention, in an opening through which the expired gas passing through the airway case is introduced and discharged, and which is disposed in the upper face of the airway case, an expired gas introducing passage functioning as the first respiratory gas flow path communicating with the expired gas guiding portion for guidingly introducing the expired gas, and an expired gas discharging passage functioning as the second respiratory gas flow path for discharging the expired gas to the outside are juxtaposed to each other. According to the configuration, the operations of attaching and detaching the expired gas guiding portion, the airway case, and the carbon dioxide sensor are facilitated, and, also when the adaptor is to be attached to a carbon dioxide nasal mask, the operations of attaching and detaching the carbon dioxide sensor can be easily performed.

According to an aspect of the invention, the configuration where the expired gas guiding portion and the airway case are detachable can be formed in a relatively simple manner, and, when the adaptor is to be attached to a carbon dioxide nasal mask, only a part of the airway adaptor is fixedly placed on the nasal mask. Therefore, a hermetical configuration can be formed in which introduction and discharge of the expired gas passing through the airway case can be surely performed inside the nasal mask without causing air leakage to the outside of the nasal mask.

According to an aspect of the invention, the nose cup for surrounding a face part in the periphery of the nostrils of the living body is fixedly placed on a part which forms the expired gas introducing passage disposed in the airway case. Even under positive pressure ventilation in CPAP or NPPV therapy which is used in treatment of a patient suffering from sleep apnea syndrome or respiratory failure, therefore, the nose cup can prevent the expired gas from the nose from being diluted by oxygen or the like which is inspired under positive pressure.

According to an aspect of the invention, the airway case is fixedly placed on an outer edge portion of a nasal mask shell of a carbon dioxide nasal mask, and the airway case is connected to the outside of the nasal mask shell, whereby a hermetical configuration can be formed in which introduction and discharge of the expired gas passing through the airway case can be surely performed inside the nasal mask without causing air leakage to the outside of the nasal mask. Therefore, the airway adaptor can be easily applied to an apparatus for CPAP or NPPV therapy which is used in treatment of a patient suffering from sleep apnea syndrome or respiratory failure.

According to an aspect of the invention, the airway adaptor has the airway case which is projected from the nasal mask. Even when the subject wears the nasal mask, therefore, the carbon dioxide sensor can be easily attached to or detached from the airway case.

According to an aspect of the invention, in the opening which is disposed in the upper face of the airway case, the expired gas introducing passage and the expired gas discharging passage are juxtaposed to each other. Therefore, it is requested that only the airway case is projected from the nasal mask. Accordingly, the airway adaptor can be applied without exerting substantial influence on the structure of an existing nasal mask. Consequently, the production cost of a nasal mask which is to be simultaneously used can be suppressed, and the airway adaptor can be applied to various kinds of nasal masks.

According to an aspect of the invention, the expired gas guiding portion is configured by the first guiding portion which guides the respiratory gas from the nostrils of the living body, and the second guiding portion which guides the respiratory gas from the mouth of the living body. Therefore, the respiratory gases from both the nose and mouth of the living body can be controlled. Furthermore, the airway adaptor can be applied also to a face mask which is widely used in respiratory therapy and the like.

What is claimed is:

1. An airway adaptor adapted to be attached to a mask, the mask adapted to be attached to a face of a living body, the airway adaptor comprising:

an airway case;

an expired gas guiding portion which is connected to the airway case to introduce a respiratory gas to the airway case;

a partition wall;

an elongated first passage adapted to introduce the respiratory gas from the expired gas guiding portion to the airway case; and an elongated second passage adapted to discharge the respiratory gas from the elongated first passage, which has been introduced to the airway case and returned in the airway case without being communicated with the expired gas guiding portion, to outside of the airway case, wherein the partition wall partitions the elongated first passage and the elongated second passage such that a portion of the elongated first passage is parallel to a portion of the elongated second passage, wherein the respiratory gas in the portion of the elongated first passage flows in a first direction and the respiratory gas in the portion of the elongated second passage flows in a second direction opposite and in reverse with respect to the first direction, wherein the airway case includes a respiratory gas flow path through which the respiratory gas passes, the respiratory gas flow path including:

the elongated first passage in which the respiratory gas flows in the first direction; and the elongated second passage in which the respiratory gas flows in the second direction opposite and in reverse with respect to the first direction, the elongated first passage and the elongated second passage being connected to each other in an opening of the airway case, and wherein, when the mask is attached to the face of the living body, at least a part of the airway case that includes the opening in which the elongated first passage and the elongated second passage are connected is projected to an outside of a shell of the mask.

2. The airway adaptor according to claim 1, wherein the expired gas guiding portion is detachably connected to the airway case.

3. The airway adaptor according to claim 1, wherein the elongated first passage and the elongated second passage are juxtaposed to each other.

4. The airway adaptor according to claim 1, wherein one of the elongated first passage and the elongated second passage surrounds the other of the elongated first passage and the elongated second passage.

5. The airway adaptor according to claim 1, wherein a nose cup for surrounding a periphery of nostrils is disposed on one of the expired gas guiding portion and the airway case.

6. The airway adaptor according to claim 1, wherein the mask is a nasal mask in which positive pressure ventilation is enabled.

7. The airway adaptor according to claim 1, wherein the expired gas guiding portion is a nasal tube which is to be inserted into nostrils of the living body.

8. The airway adaptor according to claim 1, wherein the expired gas guiding portion includes:
 a first guiding portion which guides the respiratory gas from nostrils of the living body; and
 a second guiding portion which guides the respiratory gas from a mouth of the living body.

9. The airway adaptor according to claim 8, wherein the respiratory gas which is guided by the first guiding portion and the respiratory gas which is guided by the second guiding portion are joined together in the airway case or at an upstream side of the airway case.

10. The airway adaptor according to claim 1, wherein the mask is a face mask in which positive pressure ventilation is enabled.

11. The airway adaptor according to claim 8, wherein the first guiding portion is a nasal tube which is to be inserted into the nostrils of the living body.

12. The airway adaptor according to claim 1, wherein the elongated first passage is separated from and adjacent to the elongated second passage.

13. The airway adaptor according to claim 1, wherein a portion of the elongated first passage is parallel to the entire elongated second passage.

14. The airway adaptor according to claim 1, wherein the elongated first passage is connected to the expired gas guiding portion to introduce the expiratory gas from the expired gas guiding portion to the airway case, and the elongated second passage is connected to the elongated first passage without being connected to the expired gas guiding portion to discharge the expiratory gas from the elongated first passage to the outside of the airway case.

15. The airway adaptor according to claim 1, wherein
 the partition wall is arranged between a part of the elongated first passage and a part of the elongated second passage, and
 the partition wall is defined by at least one of the part of the elongated first passage and the part of the elongated second passage.

16. The airway adaptor according to claim 1, wherein the airway case is communicated with a gas sensor configured to measure a gas in the respiratory gas.

17. The airway adaptor according to claim 16, wherein the gas sensor is a carbon dioxide sensor, and the gas to be measured includes a carbon dioxide.

18. The airway adaptor according to claim 1, wherein a part of the airway case is fixed to the shell of the mask.

19. The airway adaptor according to claim 18, wherein a part of the expired gas guiding portion is disposed in the shell of the mask.

20. A mask adapted to be attached to a face of a living body, the mask comprising:
 a shell configured to cover at least one of a nose and a mouth of the living body when the mask is attached to the face of the living body; and
 the airway adaptor of claim 1, wherein the airway adapter is attached to the shell.

21. The airway adaptor according to claim 16, wherein the airway case is in communication with the gas sensor through a tube.

* * * * *